(12) United States Patent
Kim et al.

(10) Patent No.: US 10,246,476 B2
(45) Date of Patent: Apr. 2, 2019

(54) METHOD FOR PREPARING D-PSICOSE CRYSTAL

(71) Applicant: CJ CHEILJEDANG CORPORATION, Seoul (KR)

(72) Inventors: Seong Bo Kim, Seoul (KR); Seung Won Park, Yongin-si (KR); Jun Gap An, Suwon-si (KR); Joo Hang Lee, Ansan-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/520,786

(22) PCT Filed: Aug. 9, 2015

(86) PCT No.: PCT/KR2015/009449
§ 371 (c)(1),
(2) Date: Apr. 20, 2017

(87) PCT Pub. No.: WO2016/064087
PCT Pub. Date: Apr. 28, 2016

(65) Prior Publication Data
US 2017/0313734 A1 Nov. 2, 2017

(30) Foreign Application Priority Data

Oct. 20, 2014 (KR) .................. 10-2014-0141678

(51) Int. Cl.
*B01D 9/00* (2006.01)
*C07H 1/06* (2006.01)
*C07H 3/02* (2006.01)
*B01D 15/18* (2006.01)
*B01D 15/36* (2006.01)
*A23L 27/30* (2016.01)

(52) U.S. Cl.
CPC ............ *C07H 1/06* (2013.01); *B01D 9/0013* (2013.01); *B01D 9/0036* (2013.01); *B01D 15/185* (2013.01); *B01D 15/363* (2013.01); *C07H 3/02* (2013.01); *A23L 27/33* (2016.08); *A23V 2002/00* (2013.01)

(58) Field of Classification Search
None
See application file for complete search history.

(56) References Cited

U.S. PATENT DOCUMENTS

| 3,883,365 | A | | 5/1975 | Forsberg et al. |
| 4,133,375 | A | † | 1/1979 | Ducasse |
| 2010/0204346 | A1 | | 8/2010 | Okuma et al. |
| 2011/0237790 | A1 | † | 9/2011 | Lee |
| 2012/0094940 | A1 | * | 4/2012 | Takamine .............. A23L 2/60 514/23 |

FOREIGN PATENT DOCUMENTS

| CN | 102250157 | A | | 11/2011 |
| JP | 49-1741 | A | | 1/1974 |
| JP | 50-105842 | A | | 8/1975 |
| JP | 2001-354690 | A | | 12/2001 |
| JP | 2004-533919 | A | | 11/2004 |
| JP | 2005263670 | A | † | 9/2006 |
| JP | 2011-206054 | A | | 10/2011 |
| JP | 2012-232908 | A | | 11/2012 |
| KR | 10-2009-0118465 | A | | 11/2009 |
| KR | 10-2011-0035805 | A | | 4/2011 |
| KR | 10-2011-0108185 | A | | 10/2011 |
| WO | 2006/093292 | A1 | | 9/2006 |

OTHER PUBLICATIONS

Extended European Search Report of corresponding Patent Application No. 15852095.7—10 pages (dated Jun. 19, 2018).
Matsuo et al., "Dietary D-psicose, a C-3 epimer of D-fructose, suppresses the activity of hepatic lipogenic enzymes in rats", Asia Pacific Journal of Clinical Nutrition, 2001, vol. 10, No. 3, pp. 233-237.
Matsuo et al., "D-Psicose, a rare sugar that provides no energy and additionally beneficial effects for clinical nutrition", Asia Pacific Journal of Clinical Nutrition, 2004, vol. 13, p. S127.
International Search Report dated Dec. 30, 2015 of PCT/KR2015/009449 which is the parent application and its English translation—7 pages.
Korean Office Action dated Apr. 15, 2016 of corresponding Korean Patent Application No. 10-2014-0141678—4 pages.
Korean Office Action dated Oct. 31, 2016 of corresponding Korean Patent Application No. 10-2014-0141678—10 pages.
Korean Office Action dated Mar. 31, 2017 of corresponding Korean Patent Application No. 10-2014-0141678—4 pages.
Abstract of Takeshita et al., "Mass production of D-psicose from D-fructose by a continuous bioreactor system using immobilized D-tagatose 3-epimerase", Journal of Bioscience and Bioengineering, 2000, vol. 90, Issue 4 in 1 page.
Van Duc Long et al., "Separation of D-psicose and D-fructose using simulated moving bed chromatography", 2009, J. Sep. Sci., vol. 32, pp. 1987-1995.

(Continued)

*Primary Examiner* — Layla D Berry
(74) *Attorney, Agent, or Firm* — Knobbe Martens Olson & Bear LLP

(57) ABSTRACT

A method for producing high purity D-psicose crystals having a purity of 98% (w/w) or more and a grain size of MA200 or more. The method includes: removing impurities from a D-psicose solution to obtain a purified D-psicose solution; concentrating the purified D-psicose solution; cooling the concentrated D-psicose solution to 30° C. to 40° C. through a heat exchanger; seed crystallizing the D-psicose solution at 30° C. to 40° C. to obtain a seed crystallized massecuite; and full-scale crystallizing the seed crystallized massecuite. The method can produce pure D-psicose crystals in a suitable form for industrial application through an economical crystallization process from the D-psicose solution without using organic solvents.

14 Claims, 3 Drawing Sheets

(56) References Cited

OTHER PUBLICATIONS

Takeshita et al., "Mass Production of D-Psicose from D-Fructose by a Continuous Bioreactor System Using Immobilized D-Tagatose 3-Epimerase", Journal of Bioscience and Bioengineering, 2000, vol. 90, No. 4, pp. 453-455.
Taiwanese Office Action dated Jul. 28, 2016 of corresponding Taiwanese Patent Application No. 10520922920—6 pages.
Written Opinion dated Dec. 30, 2015 of PCT/KR2015/009449 which is the parent application—4 pages.
Office Action of corresponding Japanese Patent Application No. 2017-540532—8 pages, (dated Jan. 30, 2018).

\* cited by examiner
† cited by third party

METHOD FOR PREPARING D-PSICOSE CRYSTAL

BACKGROUND

1. Technical Field

The present invention relates to a method for producing high purity D-psicose crystals from a D-psicose solution using supersaturation.

2. Description of the Related Art

It has been reported that D-psicose is a sweetener that is scarcely metabolized in the body unlike fructose or sucrose, has substantially no calories, and has little effect on body weight gain because it inhibits the formation of body fats (Matuo, T. et. *Al. Asia Pac. J. Clin. Untr.*, 10, 233-237, 2001; Matsuo, T. and K. Izumori, *Asia Pac. J. Clin. Nutri*, 13, S127, 2004).

Recently, the present inventors have reported a method for economically producing D-psicose by isomerizing D-glucose to D-fructose, followed by reacting the resultant D-fructose with immobilized cells capable of producing D-psicose epimerase (Korean Patent Application No. 10-2009-0118465). Since the reaction solutions containing D-psicose produced by the enzymatic reaction are low purity products containing D-psicose with solids content of about 20% (w/w) to about 30% (w/w), it is necessary to purify D-psicose through chromatography in order to produce D-psicose crystal particles having high purity of 98% (w/w) or more. Up to now, there is no instance showing industrially available crystallized D-psicose having high purity of 98% (w/w) or more.

In order to produce D-psicose in crystal form, there has been reported a method in which a large amount of ethanol is used after removing unreacted D-fructose in the D-psicose reaction solution via yeast fermentation (Kei T, et. al., J. Biosci. Bioeng., 90(4), 453-455, 2000). However, such a total exclusion of unreacted D-fructose from the process flow by yeast fermentation cannot achieve any cost reduction effect by reutilization of unreacted D-fructose in removing by-products. Further, the addition of a large amount of ethanol to the crystallization process can cause rise in subsidiary material costs and require facilities for the prevention of explosion and recovery of the added ethanol by a distillation method, thereby causing cost increase for preparation of D-psicose. For these reasons, the above method has a limit in mass production due to high production costs. In addition, the use of a large amount of ethanol in the crystallization of D-psicose may result in D-psicose having an ethanol odor, which is unfavorable, thereby causing a technological limitation in view of suitability for materials.

Conventional methods for crystallizing sugars can be broadly classified into two methods. One is a concentration and crystallization method and the other is a cooling crystallization method. Both methods are methods of crystallizing sugars and utilize the principle of inducing crystal growth in a metastable zone (region) of supersaturation. The concentration and crystallization method is generally used in crystallization of sugars with a high crystal growth rate such as sucrose, while the cooling crystallization method is used in crystallization of sugars with a significantly lower crystal growth rate than sucrose.

Furthermore, the methods for crystallizing sugars are performed in a metastable zone, wherein the metastable zone means that the concentration of sugar solutions exists from an equilibrium concentration, i.e. a saturated concentration to a minimum supersaturated state spontaneously precipitating crystals. A crystallization phenomenon such as crystal nucleation does not occur in this zone. When a seed crystal is added, however, crystal growth can occur, thereby increasing crystal size. Namely, when a seed is introduced into a solution exceeding saturation concentration in order to produce crystals, the seed may grow in a metastable zone, leading to crystal growth. When solutions for crystallization are excessively concentrated or rapidly cooled, the solutions become supersaturated, exceeding the metastable zone, which leads to novel crystal nucleation instead of crystal growth. Since generation of novel crystal nucleation is a factor inhibiting crystal growth due to increase in population, temperature conditions and initial entry supersaturation concentrations are important to ensure crystal growth.

D-psicose exhibits properties that hardly change in crystal generation rate and crystal growth rate in a concentration range of supersaturation, and thus can be classified as sugars that have difficult crystallization conditions for grain growth. Typically, it is known that the grain size of crystals is an important factor in sugar crystallization industries. When crystals produced in a mass production system are fine grain crystals, separation between the crystals and the mother liquor in a crystal centrifugation device is not easily performed due to viscosity of the supersaturated concentration zone, thereby deteriorating purity of final products due to the effect of the remaining mother liquor. Moreover, the remaining mother liquor can cause aggregation of crystals upon drying, thereby decreasing packaged amount of the final products or deteriorating marketability. For these reasons, the atomized crystals are not suitable for mass production.

One example of the related art is disclosed in Korean Patent Publication No. 2011-0035805A (published on Apr. 6, 2011)

BRIEF SUMMARY

Embodiments of the invention provide a method for obtaining a high purity D-psicose solution separated through continuous chromatography without yeast fermentation so that unreacted D-fructose is reusable instead of being removed from process flow.

Embodiments of the invention provide a method for producing D-psicose capable of minimizing loss of a D-psicose solution in the course of separation, drying and packaging through grain growth from the separated high purity D-psicose solution without using organic solvents such as ethanol etc., thereby facilitating separation of crystals from a mother liquor.

Embodiments of the invention provide a method for crystallizing D-psicose with reduced production cost through reduction in both variable and fixed costs.

Embodiments of the invention provide a method for producing high purity D-psicose having a purity of 98% (w/w) or more and a grain size of MA200 or more with improved crystallization process flow and product marketability.

In accordance with one embodiment, the present invention provides a method for producing high purity D-psicose crystals having a purity of 98% (w/w) or more and a grain size of MA200 or more, including: removing impurities from a D-psicose solution to obtain a purified D-psicose solution; concentrating the purified D-psicose solution; cooling the concentrated D-psicose solution to 30° C. to 40°

C. through a heat exchanger; seeding the D-psicose solution at 30° C. to 40° C. to obtain massecuite; and full-scale crystallizing the crystallized massecuite.

According to the present invention, The production method can produce pure D-psicose crystals in a suitable form for industrial application through an economical crystallization process from a D-psicose solution without organic solvents.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Figure 1:
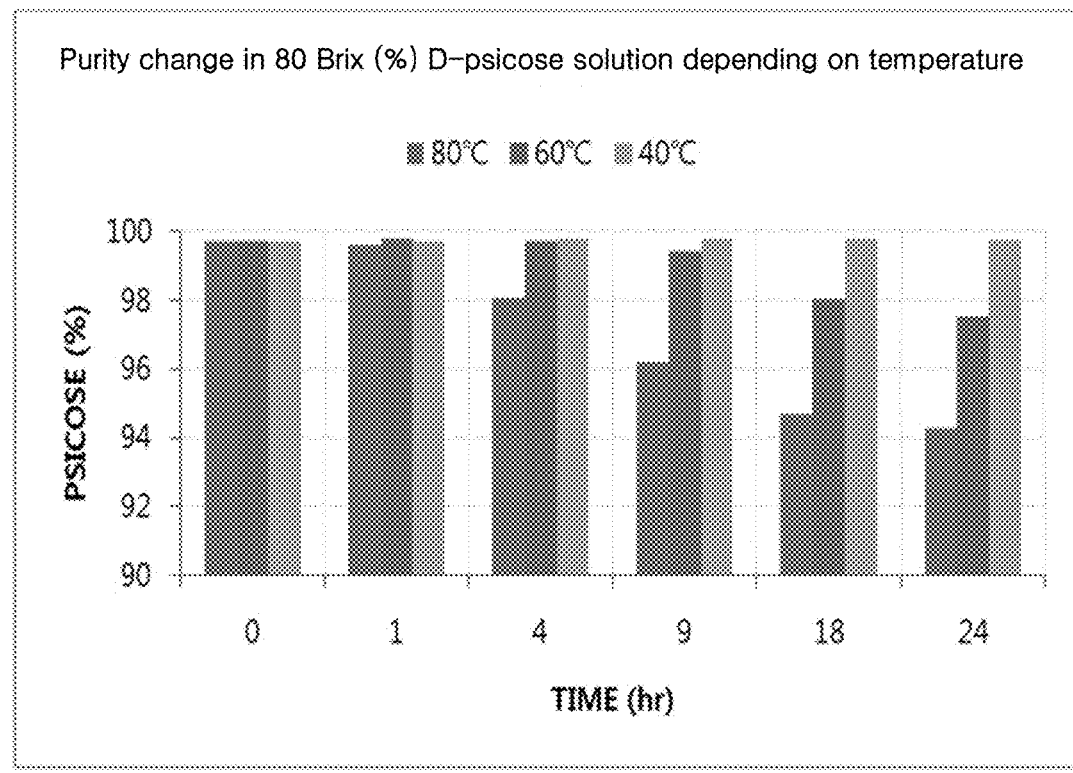
FIG. 1 shows heat denatured purity changes in an 80 Brix (%) D-psicose solution depending on temperatures.
Figure 2:
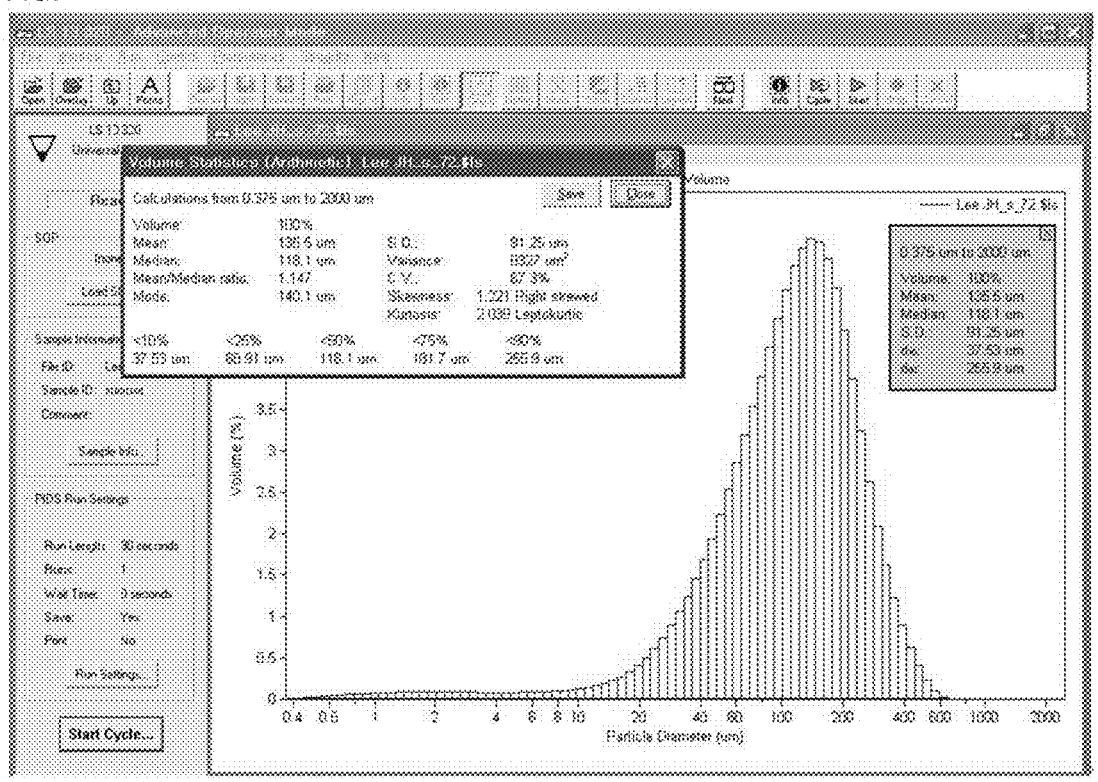
FIG. 2 is a graph depicting the grain size (particle diameter) of D-psicose prepared from seed crystallization.
Figure 3:
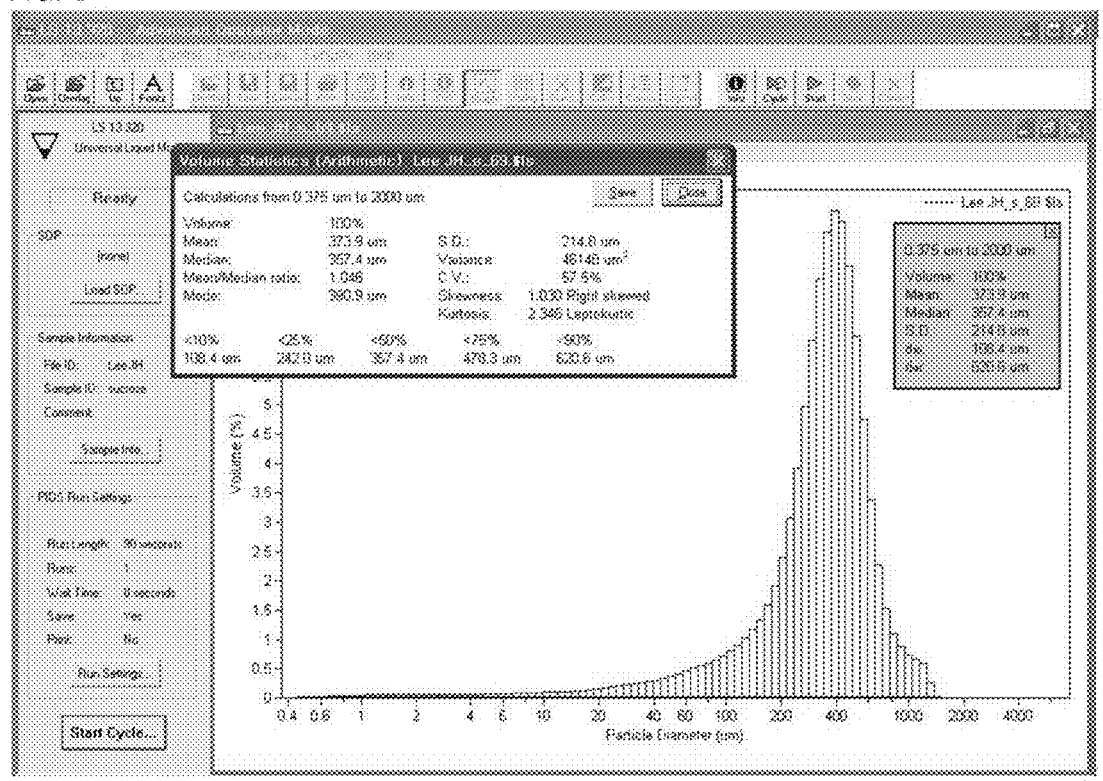
FIG. 3 is a graph depicting the grain size (particle diameter) of D-psicose prepared via full-scale crystallization.

Next, embodiments of the present invention will be described in more detail. Descriptions of details apparent to those skilled in the art will be omitted herein.

One embodiment of the present invention relates to a method for producing D-psicose crystals having a high purity of 98% (w/w) or more and a grain size of MA200 or more, including: removing impurities from a D-psicose solution to obtain a purified D-psicose solution; concentrating the purified D-psicose solution; cooling the concentrated D-psicose solution to 30° C. to 40° C., preferably 35° C. to 40° C., through a heat exchanger; seed crystallizing the D-psicose solution at 30° C. to 40° C. to obtain massecuite; and full-scale crystallizing the seed crystallized massecuite.

The D-psicose solution used in the present invention may be produced by microorganisms belonging to genus *Corynebacterium* capable of expressing D-psicose epimerase from D-fructose or D-psicose epimerase isolated from genus *Corynebacterium*. The term "D-psicose epimerase" refers to D-psicose-3-epimerase capable of converting D-fructose into D-psicose.

The D-psicose solution may be obtained by culturing *Corynebacterium glutamicum* KCTC 13032 capable of producing D-psicose epimerase, immobilizing the obtained microorganism or an enzyme isolated from the microorganism on an immobilizing carrier such as sodium alginate, and introducing D-fructose as a substituent, as disclosed in Korean Patent Application No. 2009-0118465, without being limited thereto.

In order to harvest D-psicose crystals from the D-psicose solution, other substances affecting purification and crystallization of D-psicose are removed from the D-psicose solution such that the D-psicose solution has a suitable state for efficient crystallization. Accordingly, the method for producing D-psicose crystals according to the present invention may include removing impurities from the D-psicose solution to obtain a purified D-psicose solution.

Specifically, the step of obtaining the purified D-psicose solution may include decoloring the D-psicose solution by passing through a column packed with a decoloring agent; desalting the decolored D-psicose solution by ion exchange resin chromatography; and passing the desalted D-psicose solution through a continuous chromatography column packed with an ion exchange resin to which potassium activating groups are attached, thereby obtaining purified D-psicose solution.

More specifically, the step of desalting the D-psicose solution may be performed by a chromatographic method by passing the D-psicose solution through a column packed with a cation exchange resin and a column packed with an anion exchange resin. When a strong basic anion resin is used in ion exchange resin purification to produce the purified D-psicose solution, D-psicose can be denatured, causing decrease in purity of D-psicose solution. Thus, in order to produce high purity D-psicose crystals, it is necessary to use 100% weak alkaline anion resin. The denaturing of D-psicose is also observed in a mixed resin consisting of a strong acidic cation resin and a strong alkaline anion resin typically used in sugar purification. Thus, in order to perform effective desalting without denaturing D-psicose, 100% weak alkaline anion resin is used in desalting the D-psicose solution.

Further, in order to obtain high purity D-psicose, separation through continuous chromatography may be performed. The content of D-psicose in the D-psicose solution for D-psicose crystals is preferably 90% to 95% or more, more preferably 95% or more. Since D-psicose in the D-psicose solution prepared by D-psicose epimerase has a low purity of about 24% (w/w), direct crystallization from the D-psicose solution cannot be performed. In order to obtain high purity D-psicose crystals, the D-psicose solution is subjected to decoloring and desalting to remove impurities prior to crystallization, followed by purifying through a continuous chromatography column packed with an ion exchange resin to which calcium activating groups are attached.

In a typical method for crystallizing sugars, the D-psicose solution is slowly cooled from high temperature to a certain temperature range at a specific rate per hour within a supersaturated concentration range. Unlike such a typical method, in the method for producing D-psicose crystals according to the present invention, the D-psicose solution concentrated to a supersaturated concentration in the range of 80 to 85 Brix (%) (D-psicose solution×100/total solution) is rapidly cooled through a heat exchanger to a temperature of 30° C. to 40° C. at a rate of 5° C. to 20° C. per hour, and then introduced into a crystallization device. When the D-psicose solution is cooled to 30° C. to 40° C., the D-psicose solution concentrated to a supersaturated concentration in the range of 80 to 85 Brix (%) (D-psicose solution×100/total solution) can be prevented from heat denaturing, whereby the purity of the separated high purity D-psicose solution can be preserved, thereby providing improvement in yield and grain size of crystals upon crystallization process. In order to transfer the D-psicose solution concentrated to a supersaturated concentration in the range of 80 to 85 Brix (%) (D-psicose solution×100/total solution) to the crystallization device, the D-psicose solution concentrated to a supersaturated concentration in the range of 80 to 85 Brix (%) is collected and stored in a middle storage tank, the temperature of which is 60° C. to 75° C. corresponding to a heat denaturing temperature for D-psicose.

Specifically, the time for crystallizing D-psicose is 80 hours to 120 hours. Crystallization of D-psicose may be performed by rapidly cooling the concentrated D-psicose solution within a supersaturated concentration range to 30° C. to 40° C. at a rate of 5° C. to 20° C. per hour through a heat exchanger, followed by introducing the D-psicose solution into the crystallization device, and repeatedly heating and cooling the D-psicose solution within the crystallization temperature range of 30° C. to 40° C. for 5 to 10 times. Namely, the D-psicose solution concentrated to a supersaturated concentration range of 80 to 85 Brix (%) at 30° C. to 40° C. is introduced in an amount of 5% (v/v) to 20% (v/v) based on the operation capacity of the crystallization device, in which the cooling water is circulated within the temperature range of 30° C. to 35° C. Crystallization of D-psicose is initiated by introducing the prepared D-psicose seed in an amount of 10 ppm to 100 ppm (v/v) based on an initial amount of the D-psicose to obtain massecuite. Herein, the term "massecuite" refers to a mixed slurry consisting of crystals and solutions when the D-psicose seed triggers crystallization.

Furthermore, in order to induce growth of D-psicose crystals, the D-psicose solution concentrated to a supersaturated concentration range of 80 to 85 Brix (%) at 30° C. to 40° C. is introduced in an amount of 5% (v/v) to 20% (v/v) based on the operation capacity of the crystallization device per 10 hours to 20 hours from initiation of crystallization to the crystallization device. Such manipulation may be repeated 5 times to 10 times such that heating and cooling are repeated 5 times to 10 times within the commodity temperature ranging from 30° C. to 40° C. inside the crystal massecuite, thereby inducing growth of the D-psicose crystals.

The D-psicose crystals obtained by the production method according to the present invention specifically have a grain size of MA 200 or more, more specifically a grain size of MA 300 or more.

As used herein, the grain size refers to an average size of crystals. In accordance with JIS or ASTM, the grain size is represented by the number of grains per unit area (25 mm$^2$) in a photomicrograph taken at 100×, which is also called grain size number. Recently, the grain size is employed to mean an average size of crystals. In the present invention, the grain size refers to an average size (particle diameter) of crystals.

Methods for measuring the grain size of D-psicose are not particularly limited, and any methods typically used in the art can be employed. Examples of the method for measuring grain size include a comparison procedure (FGC), a planimetric procedure (FGI), and an intercept procedure (FGP), without being limited thereto.

In order to obtain D-psicose crystals having a grain size of MA 200 or more, crystallization may be performed through two stages, i.e. seed crystallization and full-scale crystallization, wherein the seed crystallization is preferably performed in an amount of 5% (v/v) to 20% (v/v) as compared with full-scale crystallization. The grain size for the seed crystals prepared by the method according to the present invention ranges from MA 100 to MA 150. The entire amount of the prepared seed crystals is transferred to a device for full-scale crystallization, followed by conducting full-scale crystallization in the same manner as above, thereby finally obtaining high purity D-psicose having a purity of 98% (w/w) or more and a grain size of MA 200 or more, more preferably MA 300 or more.

As the crystallization device, any sugar crystallization device typically used in the art may be used without change or with suitable modification. As a device for separating high purity D-psicose crystals and the mother liquor from the final crystal massecuite, any sugar separation device typically used in the art may be used without change or with suitable modification.

Hereinafter, the present invention will be described in more detail with reference to some examples. It should be understood that these examples are provided for illustration only and are not to be construed in any way as limiting the present invention.

Descriptions of details apparent to those skilled in the art will be omitted herein.

EXAMPLES

Preparative Example

As disclosed in Korean Patent Application No. 10-2009-0118465, D-psicose was produced by a method for continuously producing D-psicose, including fermentation of *Corynebacterium glutamicum* KCTC 13032 and conversion of D-fructose into D-psicose by means of carriers to which the above microorganism or D-psicose epimerase separated from the microorganism is immobilized. D-psicose prepared by the method had a low purity of about 24% (w/w), thereby making it difficult to perform direct crystallization. The produced D-psicose solution was concentrated to 50 Brix (%) and passed through a decoloring column packed with granulated activated carbon in order to remove colored substances from the concentrated solution.

Example 1

The resulting D-psicose solution obtained in Preparation Example has a purity of 24% (w/w), which should be increased to 90% to 95% (w/w) or more in order to perform crystallization. For efficient separation of D-psicose through continuous chromatography, ions in the D-psicose solution should be removed. When ion components are present in the solution to be separated, the ion components can replace the activating groups of the separation resin, lowering the separation capability of the resin, which in turn makes it impossible to perform the continuous separation of D-psicose to a purity of 90% to 95% (w/w) or more by using the separation resin.

Accordingly, the D-psicose solution having a purity of 24% (w/w) obtained in Preparation Example was passed through a column packed with a strong acidic cation exchange resin (Bayer S1668) substituted with hydrogen groups and a column packed with a weak basic anionic exchange resin (Bayer Bayer S4528) substituted with hydroxyl groups, thereby removing ion components remaining in the solution. Removal of the ion components was measured using a conductivity meter, wherein conductivity was adjusted to not more than 10 microsiemens per cm, and the purity of D-psicose was maintained at 24% (w/w). A commercially available weak anion exchange resin partially retains strong basic properties. Thus, in order to perform desalting without loss of D-psicose due to purity decrease, 100% weak basic anion resin having no strong basic properties should be used.

Example 2

The D-psicose solution having a purity of 24% (w/w) obtained in Example 1 by removing colored materials and ionic components through decoloring and desalting was concentrated to 60 Brix (%). The concentrated D-psicose was passed through an ion exchange resin (Amberlite CR1310 Ca) substituted with calcium groups by means of ASMB 6 Tower (manufactured by Organo Co., Ltd.) to yield a purified D-psicose solution. The amount of the ion exchange resin packed in the ion exchange resin column was 10 L. The amount of the sample passed through the column, namely, the purified D-psicose solution prepared in Example 1, was 2 L/cycle, and the operation temperature was 60° C. After introducing the sample and elution with 5 L/cycle of deionized water, the resulting D-psicose had a purity of 95% (w/w).

Example 3

The D-psicose solution having a purity of 95% (w/w) purified and separated in Example 2 was concentrated to 80 Brix (%). The D-psicose solution having a purity of 95% (w/w) was rapidly cooled to 40° C. at a rate of 10° C. per hour through a heat exchanger and introduced into a crystallization device in an amount of 20% (v/v) based on the operation capacity of the crystallization device. The cooling water in the crystallization device was circulated to maintain 35° C. Then, the prepared D-psicose seed was introduced in an amount of 100 ppm (v/v) to initiate D-psicose seed crystallization. In order to induce growth of D-psicose crystals, the D-psicose solution concentrated to 80.0 Brix (%) at 40° C. was further added in an amount of 20% (v/v) based on the operation capacity of the crystallization device per 12 hours from initiation of crystallization to the crystallization device. Such manipulation was repeated 4 times such that heating and cooling were repeated 4 times within the commodity temperature range from 35° C. to 40° C. inside the crystal massecuite. Finally, D-psicose seed crystal reaction was conducted from initiation of crystallization for 60 hours. D-psicose seed crystallized massecuite was separated, dried and sieved by a crystal centrifuge device through separation of D-psicose crystals and a mother liquor to yield final D-psicose crystals having a purity of 99.4% (w/w) and a grain size of MA 135.5 with yield of 35.2%.

Example 4

Full-scale crystallization of D-psicose was performed using D-psicose seed crystallized massecuite prepared in Example 3. D-psicose seed crystallized massecuite was introduced into a crystallization device in an amount of 20% (v/v) based on the operation capacity of the crystallization device. In the crystallization device, cooling water was circulated to maintain 35° C. The D-psicose solution having a purity of 95% (w/w) purified and separated in Example 2 was concentrated to 80 Brix (%). The D-psicose solution having a purity of 95% (w/w) was rapidly cooled to 40° C. at a rate of 10° C. per hour through a heat exchanger. Then, the cooled D-psicose solution was introduced into the crystallization device in an amount of 20% (v/v) based on the operation capacity of the crystallization device such that the initial total amount for full-scale crystallization became 40% (v/v) based on the operation capacity of the crystallization device. In order to induce growth of D-psicose crystals, the D-psicose solution concentrated to 80.0 Brix (%) at 40° C. was further added in an amount of 20% (v/v) based on the operation capacity of the crystallization device per 20 hours from initiation of crystallization to the crystallization device. Such manipulation may be repeated 3 times so that heating and cooling are repeated 3 times within the commodity temperature range from 35° C. to 40° C. within the crystal massecuite. Finally, full-scale D-psicose crystallization was conducted for 80 hours. D-psicose seed crystallized massecuite was separated, dried and sieved by a crystal centrifuge device through separation of D-psicose crystals and a mother liquorto yield final D-psicose crystals having a purity of 99.8% (w/w) and a grain size of MA 373.9 with yield of 52.8%.

Comparative Example 1

The D-psicose solution having a purity of 24% (w/w) obtained in Preparation Example was passed through a column packed with a strong acidic cation exchange resin (Bayer S1668) substituted with hydrogen groups and a column packed with a weak basic anion exchange resin (Bayer Bayer S4528) substituted with hydroxyl groups. Finally, the resulting D-psicose solution was passed through an ion exchange column (Bayer NM60) packed with a mixture of a strong acidic cation exchange resin and a strong basic anion exchange resin, thereby removing ion components remaining in the solution. Removal of the ion components was identified using a conductivity meter, wherein the conductivity was adjusted to not more than 10 microsiemens per cm, and the purity of D-psicose was decreased to 21.2% (w/w).

Comparative Example 2

The D-psicose solution having a purity of 24% (w/w) obtained in Preparation Example was passed through a column packed with a strong acidic cation exchange resin (Bayer S1668) substituted with hydrogen groups and a column packed with a weak basic anion exchange resin (Bayer S4528) substituted with hydroxyl groups, thereby removing ion components remaining in the solution. The removal of the ion components was identified using a conductivity meter, wherein the conductivity was adjusted to not more than 10 microsiemens per cm, and the purity of D-psicose was decreased to 22.8% (w/w).

Comparative Example 3

The D-psicose solution having a purity of 95% (w/w) purified and separated in the above Example 2 was concentrated to 85 Brix (%). The D-psicose solution having a purity of 95% (w/w) in the crystallization device was cooled from 50° C. to 35° C. at a rate of 0.31° C. per hour for 48 hours to perform crystallization. The final D-psicose crystal massecuite was separated through the separation of D-psicose crystals and the mother liquor using a crystal centrifuge device. As a result, there was no separation between D-psicose crystals and the mother liquor in the final crystal massecuite.

Comparative Example 4

The D-psicose solution having a purity of 95% (w/w) purified and separated in the above Example 2 was concentrated to 82.5 Brix (%). The D-psicose solution having a purity of 95% (w/w) in the crystallization device was cooled from 50° C. to 35° C. at a rate of 0.30° C. per hour for 50 hours to perform crystallization. The final D-psicose crystal massecuite was separated, dried and sieved by a crystal centrifuge device through separation of D-psicose crystals and the mother liquor to yield final D-psicose crystals having a purity of 98.5% (w/w) and a grain size of MA 82 with yield of 20.9%.

Comparative Example 5

The D-psicose solution having a purity of 95% (w/w) purified and separated in the above Example 2 was concentrated to 82.5 Brix (%). The D-psicose solution having a purity of 95% (w/w) in the crystallization device was cooled from 50° C. to 35° C. at a rate of 0.15° C. per hour for 100 hours to perform crystallization. The final D-psicose crystal massecuite was separated, dried and sieved by a crystal centrifuge device through separation of D-psicose crystals and the mother liquor to yield final D-psicose crystals having a purity of 98.9% (w/w) and a grain size of MA 95 with yield of 24.5%.

Comparative Example 6

The D-psicose solution having a purity of 95% (w/w) purified and separated in the above Example 2 was concentrated to 82.5 Brix (%). The D-psicose solution having a purity of 95% (w/w) in the crystallization device was cooled from 50° C. to 35° C. at a rate of 0.08° C. per hour for 200 hours to perform crystallization. The final D-psicose crystal massecuite was separated, dried and sieved by a crystal centrifuge device through separation of D-psicose crystals and the mother liquor to yield final D-psicose crystals having a purity of 97.9% (w/w) and a grain size of MA 75 with yield of 17.2%.

The purity of D-psicose prepared in Comparative Examples 1 and 2 wherein the strong acidic ion exchange resin was used in Comparative Example 1 and commercially available weak basic ion exchange resin except for 100% weak basic ion exchange resin was used in Comparative Example 2 was lower than the purity of D-psicose prepared in Example 1. Further, Comparative Examples 1 to 3 wherein conventional sugar crystallization methods, i.e. methods of slowly cooling the D-psicose solution from high temperature to a certain temperature range at a specific rate per hour for supersaturated concentration were employed did not show separation between D-psicose crystals and the mother liquor, or exhibited lower purity, grain size and yield, as compared with those of Examples. From these results, it can be seen that the method for preparing D-psicose crystals according to the present invention can produce D-psicose with better marketability as compared with existing cooling crystallization methods.

Although some embodiments have been described herein, it should be understood by those skilled in the art that these embodiments are given by way of illustration only, and that various modifications, variations, and alterations can be made without departing from the spirit and scope of the invention. Therefore, the scope of the invention should be limited only by the accompanying claims and equivalents thereof.

What is claimed is:

1. A method for producing D-psicose crystals having a grain size of MA200 μm or larger, comprising:
   removing impurities from a D-psicose solution to obtain a purified D-psicose solution;
   concentrating the purified D-psicose solution to provide a concentrated D-psicose solution having a concentration of 80 Brix (%) to 85 Brix (%);
   performing rapid cooling of the concentrated D-psicose solution to 30° C. to 40° C. in a heat exchanger to provide a copied D-psicose solution having a temperature between 3° C. and 4° C., wherein the rapid cooling is performed at a cooling rate of 5° C. to 20° C. per hour;
   placing the cooled D-psicose solution at a temperature between 30° C. and 40° C. to a crystallizer and adding D-psicose seed crystals to the crystallizer;
   performing seeded crystallization of D-psicose in the crystallizer while controlling temperature to stay between 30° C. and 40° C., which provides a D-psicose massecuite having a temperature between 30° C. and 40° C.; and
   performing full-scale crystallization of D-psicose using the D-psicose massecuite while controlling temperature to stay between 30° C. and 40° C., which provides D-psicose crystals having a grain size of MA200 μm or larger.

2. The method according to claim 1, wherein the step of removing impurities from a D-psicose solution to obtain a purified D-psicose solution comprises:
   decoloring the D-psicose solution by passing through a column packed with a decoloring agent;
   desalting the decolored D-psicose solution via ion exchange resin chromatography; and
   passing the desalted D-psicose solution through a continuous chromatography column packed with an ion exchange resin to which calcium activating groups are attached.

3. The method according to claim 2, wherein the ion exchange resin used in the ion exchange resin chromatography is a 100% weak basic anion resin.

4. The method according to claim 2, wherein the step of passing through a continuous chromatography column is a simulated moving bed (SMB) process.

5. The method according to claim 2, wherein the D-psicose solution purified through the continuous chromatography column has a purity of 95% (w/w) or more.

6. The method for producing high purity D-psicose crystals according to claim 1, wherein performing seeded crystallization comprises
   adding seeds of D-psicose to the cooled D-psicose solution at a temperature between 30° C. and 40° C.; and
   adding additional D-psicose solutions to the seeds-added D-psicose solution.

7. The method according to claim 6, wherein the concentration of the additional D-psicose solutions is in a range of 80 Brix (%) to 85 Brix (%).

8. The method according to claim 6, wherein the volume of the additional D-psicose solutions is in a range of 5 (v/v) % to 20 (v/v) % based on the volume of the seed-added D-psicose solution.

9. The method according to claim 1, wherein the full-scale crystallization comprises:
   adding another D-psicose solution having a purity of 95% (w/w) or higher and a concentration of 80 Brix (%) to 85 Brix (%) to the seed crystallized massecuite, and
   subsequently, repeating heating and cooling the resulting solution within the range of 30° C. to 40° C.

10. The method according to claim 9, wherein repeating heating and cooling the resulting solution comprises adding, to the resulting solution, an additional D-psicose solution at a temperature of 30° C. to 40° C. two times or more an interval of 10 hours to 20 hours.

11. The method according to claim 10, wherein the additional D-psicose solution is added each time in an amount of 5 (v/v) % to 20 (v/v) % based on the volume of the resulting solution to which the additional D-psicose solution is added.

12. A method of crystallizing D-psicose, the method comprising:
   concentrating a D-psicose solution to provide a concentrated D-psicose solution having a concentration of 80 Brix (%) to 85 Brix (%);
   performing rapid cooling of the concentrated D-psicose solution to 30° C. to 40° C. to provide a cooled D-psicose solution having a temperature between 30°

C. and 40° C., wherein the rapid cooling is performed by heat exchange at a cooling rate of 5° C. to 20° C. per hour;

placing, in a first crystallizer, the cooled D-psicose solution having a temperature between 30° C. and 40° C. and adding D-psicose crystal seeds to the first crystallizer;

performing seeded crystallization of D-psicose in the first crystallizer while controlling a temperature of the D-psicose solution in the first crystallizer to stay between 30° C. and 40° C., which provides a D-psicose massecuite;

placing the D-psicose massecuite to a second crystallizer and adding thereto a processed D-psicose solution to provide a crystallization mixture in the second crystallizer, wherein the processed D-psicose has a concentration between 80 Brix (%) and 85 Brix (%) and a temperature between 30° C. and 40°; and performing crystallization of D-psicose in the second crystallizer while controlling a temperature of the crystallization mixture in the crystallizer to stay between 30° C. and 40° C., which provides D-psicose crystals having a grain size of MA200 μm or larger.

13. The method of claim 12, wherein performing seeded crystallization in the first crystallizer comprises adding an additional D-psicose solution to the first crystallizer at least once, wherein the additional D-psicose solution is at a temperature between 30° C. and 40° C. when added.

14. The method of claim 12, wherein performing crystallization in the second crystallizer comprises adding an additional D-psicose solution to the second crystallizer at least once, wherein the additional D-psicose solution is at a temperature between 30° C. and 40° C. when added.

* * * * *

UNITED STATES PATENT AND TRADEMARK OFFICE
CERTIFICATE OF CORRECTION

| | |
|---|---|
| PATENT NO. | : 10,246,476 B2 |
| APPLICATION NO. | : 15/520786 |
| DATED | : April 2, 2019 |
| INVENTOR(S) | : Seong Bo Kim et al. |

It is certified that error appears in the above-identified patent and that said Letters Patent is hereby corrected as shown below:

In the Specification

In Column 1 at Line 19, change "*Nutri,.*" to --*Nutr.,*--.

In Column 2 at Line 37, change "*2011)*" to --*2011).*--.

In Column 3 at Line 4, change "*The*" to --*the*--.

In Column 6 at Line 44, change "*(Bayer Bayer*" to --*(Bayer*--.

In Column 8 at Line 8, change "*(Bayer Bayer*" to --*(Bayer*--.

In the Claims

In Column 9 at Line 59, in Claim 1, change "*copied*" to --*cooled*--.

In Column 9 at Line 60, in Claim 1, change "3° C. and 4° C.," to --*30°C. and 40°C.,*--.

In Column 11 at the last line, in Claim 12, change "40°;" to --*40°C.;*--.

Signed and Sealed this
Thirtieth Day of July, 2019

Andrei Iancu
*Director of the United States Patent and Trademark Office*